United States Patent [19]
Subramanian

[11] Patent Number: 6,087,543
[45] Date of Patent: Jul. 11, 2000

[54] FLUORINATED BENZENE MANUFACTURING PROCESS

[75] Inventor: Munirpallam A. Subramanian, Kennett Square, Pa.

[73] Assignee: E. I. du Pont de Nemours and Company, Wilmington, Del.

[21] Appl. No.: 09/360,977

[22] Filed: Jul. 27, 1999

Related U.S. Application Data

[60] Provisional application No. 60/094,386, Jul. 28, 1998.

[51] Int. Cl.$^7$ ................................................... C07C 17/20
[52] U.S. Cl. ................................................................. 570/147
[58] Field of Search ............................................. 570/147

[56] References Cited

U.S. PATENT DOCUMENTS 3,277,192  10/1966  Fielding et al. ........................ 570/147
4,394,527  7/1983  Fischer et al. ........................ 570/147

*Primary Examiner*—Alan Siegel

[57] ABSTRACT

A process is disclosed for producing fluorinated benzene. The process involves (a) contacting chlorobenzene starting material with a metal fluoride composition of the formula $(AgF)(MF_2)_x$ (where M is Mn, Fe, Co, Ni, Cu, Zn or a mixture thereof and x is a number between 0 and 1) at a temperature above 175° C. sufficient to remove the chlorine substituent from the starting material and to transfer F from the metal fluoride composition to the starting material (thereby producing a reduced metal fluoride composition comprising a silver component of the formula $AgF_{1-y}$ where y is a number from 0.01 to 1); (b) oxidizing the reduced metal fluoride composition from (a) in the presence of HF to regenerate the metal fluoride mixture composition of the formula $(AgF)(MF_2)_x$; and (c) recycling regenerated metal fluoride composition of (b) to (a).

2 Claims, No Drawings

FLUORINATED BENZENE MANUFACTURING PROCESS

This application claims the priority benefit of U.S. Provision Application 60/094,386, filed Jul. 28, 1998.

FIELD OF THE INVENTION

This invention relates to a process for the manufacture of fluorobenzene by contacting chlorobenzene with argentous fluoride.

BACKGROUND

Fluorobenzene, an agricultural chemicals intermediate, is typically produced by the reaction of aniline and sodium nitrite in the presence of hydrogen fluoride. A diazonium salt intermediate is formed during this process which because of its instability adds to the cost of manufacture. U.S. Pat. No. 4,394,527 discloses a process for monofluorinating a benzene nucleus comprising reacting a benzene compound in the liquid phase with argentic fluoride which is reduced to argentous fluoride during the reaction.

There is still a need for an efficient commercial process for preparing fluorobenzene using less expensive materials.

SUMMARY OF THE INVENTION

A process is provided for producing fluorinated benzene. The process comprises (a) contacting chlorobenzene starting material with a metal fluoride composition of the formula $(AgF)(F_2)_x$ where M is selected from the group consisting of Mn, Fe, Co, Ni, Cu, Zn and mixtures thereof and wherein x is a number between 0 and 1, at a temperature above 175° C. sufficient to remove the chlorine substituent from the starting material and to transfer F from the metal fluoride composition to the starting material, thereby producing a reduced metal fluoride composition comprising a silver component of the formula $AgF_{1-y}$ where y is a number from 0.01 to 1; (b) oxidizing the reduced metal fluoride composition from (a) in the presence of HF to regenerate the metal fluoride mixture composition of the formula $(AgF)(MF_2)_x$; and (c) recycling regenerated metal fluoride composition of (b) to (a).

DETAILED DESCRIPTION

An important aspect of this invention involves the reaction of a metal fluoride composition of the formula $(AgF)(MF_2)_x$, where M and x are as defined above, with chlorobenzene to produce fluorobenzene. In an embodiment of this invention chlorobenzene is passed over the regenerable reagent, argentous fluoride (AgF), at reaction conditions until the conversion rate to fluorobenzene is reduced to an economically insufficient level. The contacting of chlorobenzene ($C_6H_5Cl$) with argentous fluoride is done in the vapor phase at a temperature from about 175° C. to about 220° C., preferably from about 200° C. to about 220° C. As the reaction temperature is raised above 220° C., the fluorobenzene ($C_6H_5F$) is further fluorinated and difluorobenzene ($C_6H_4F_2$), trifluorobenzene ($C_6H_3F_3$) and tetrafluorobenzene ($C_6H_2F_4$) are produced.

In a second embodiment, chlorobenzene is passed over the regenerable reagent, $(AgF)(MF_2)_x$, at reaction conditions until the conversion rate to fluorobenzene is reduced to an economically insufficient level. With this second reagent the contacting with chlorobenzene is also done in the vapor phase, but at a temperature of from about 250° C. to 450° C., preferably from about 275° C. to about 325° C. As the reaction temperature is raised above 300° C., the fluorobenzene ($C_6H_5F$) is further fluorinated and difluorobenzene ($C_6H_4F_2$), trifluorobenzene ($C_6H_3F_3$) and tetrafluorobenzene ($C_6H_2F_4$) are produced.

The $(AgF)(W_2)_x$ functions as a regenerable fluorinating reagent (i.e., the reduced metal fluoride composition comprising a reduced form of silver such as metallic silver can be oxidized back to $(AgF)(MF_2)_x$). The argentous fluoride (AgF) can be used by itself or as part of a mixture. The metal fluoride mixtures of this invention, $(AgF)(MF_2)_x$ where M is selected from the group consisting of Mn, Fe, Co, Ni, Cu, Zn and/or mixtures thereof and wherein x is a number between 0 and 1 can be prepared by conventional engineering mixing techniques using the metal fluoride powder(s). Mixed metal compounds such as $AgMnF_3$, $AgFeF_3$, $AgCOF_3$, $AgNiF_3$, $AgCuF_3$ and $AgZnF_3$ can be prepared by heating a 1:1 molar mixture of AgF and $ME_2$, where M is as defined above, to between from about 400° C. to about 450° C. for about at least one hour in an inert atmosphere (e.g., nitrogen or argon). The powders may be made into granules or pellets.

The contact time is typically from about 1 to about 120 seconds (e.g., from about 5 to 60 seconds).

The reaction can also be done in the presence of inert gases which are stable under the reaction conditions such as nitrogen and argon.

Unreacted chlorobenzene can be recycled to the reactor for the production of additional fluorobenzene. The fluorobenzene may be recovered from the reaction product and any unreacted benzene by conventional procedures such as distillation.

Argentous fluoride can be regenerated from the fluoride-depleted reagent either by reacting with oxygen and HF at a temperature between about 250° C. to about 500° C. or by converting the fluoride-depleted reagent to a stable salt (e.g, $AgNO_3$) and reacting said salt with HF. The oxygen may be diluted with inert gases such nitrogen and argon.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following embodiments are to be construed as illustrative, and not as constraining the remainder of the disclosure in any way whatsoever.

EXAMPLES

Example 1

Preparation of Fluorobenzene

An Inconel® nickel alloy tube reactor was packed with argentous fluoride (AgF, 5 g). The catalyst was heated to reaction temperature under a nitrogen flow. The nitrogen flow was adjusted to 30 cc/min. passed through chlorobenzene over the catalyst. Reaction products were analyzed using a Hewlett Packard 6890 Gas Chromatograph/5973 Mass Spectrometer. All analyses are reported in area% and shown in Table 1.

TABLE 1

| Run No. | T (° C.) | % $C_6H_5Cl$ | % $C_6H_5F$ | % $C_6H_4F_2$ | % $C_6H_3F_3$ | % $C_6H_2F_4$ |
|---|---|---|---|---|---|---|
| 1 | 200 | 75.1 | 20.4 | — | — | — |
| 2 | 210 | 77.3 | 22.7 | — | — | — |
| 3 | 220 | 68.7 | 26.3 | 5 | — | — |
| 4 | 230 | 60.5 | 33.5 | 6 | — | — |
| 5 | 240 | 42.8 | 47 | 10.2 | — | — |
| 6 | 250 | 28.5 | 56.7 | 9.6 | — | — |
| 7 | 260 | 9.4 | 70.1 | 20.5 | — | — |
| 8 | 270 | 4.2 | 67 | 28.7 | — | — |
| 9 | 280 | <0.1 | 58.8 | 36.2 | 5 | — |
| 10 | 290 | <0.1 | 52.2 | 41 | 6.8 | <0.1 |
| 11 | 300 | <0.1 | 45.5 | 46.3 | 8.2 | <0.1 |
| 12 | 310 | <0.1 | 37.4 | 49.1 | 13.6 | <0.1 |

Example 2

An Inconel® nickel alloy tube reactor was packed with $AgCuF_3$ (5 g). The catalyst was heated to reaction temperature under a nitrogen flow. The nitrogen flow was adjusted to 30 cc/min. and passed through chlorobenzene over the catalyst. Reaction products were analyzed using a Hewlett Packard 6890 Gas Chromatograph/5973 Mass Spectrometer. All analyses are reported in area% and are shown in Table 2.

TABLE 2

| Run No. | T (° C.) | % $C_6H_5Cl$ | % $C_6H_5F$ | % $C_6H_4F_2$ | % $C_6H_4ClF$ | % $C_6H_2F_4$ |
|---|---|---|---|---|---|---|
| 1 | 250 | 99.9 | <0.1 | — | — | — |
| 2 | 300 | 84.2 | 15.8 | — | <0.1 | — |
| 3 | 350 | 44.8 | 34.8 | 9.9 | 1.7 | — |
| 4 | 400 | 23.2 | 39 | 37.8 | <0.1 | — |
| 5 | 450 | 21.2 | 29 | 44.9 | — | 5[a] |

[a]$C_6H_3F_3$ (<0.1%) was also detected

I claim:

1. A process for producing fluorinated benzene, comprising:

(a) contacting chlorobenzene starting material with a metal fluoride composition of the formula $(AgF)(NF_2)_x$ where M is selected from the group consisting of Mn, Fe, Co, Ni, Cu, Zn and mixtures thereof and wherein x is a number between 0 and 1, at a temperature above 175° C. sufficient to remove the chlorine substituent from the starting material and to transfer F from the metal fluoride composition to the starting material, thereby producing a reduced metal fluoride composition comprising a silver component of the formula $AgF_{1-y}$ where y is a number from 0.01 to 1;

(b) oxidizing the reduced metal fluoride composition from (a) in the presence of HF to regenerate the metal fluoride mixture composition of the formula $(AgF)(W_2)_x$; and (c) recycling regenerated metal fluoride composition of (b) to (a).

2. The process of claim 1 wherein fluorobenzene is produced by contacting chlorobenzene with argentous fluoride.

* * * * *